US00PP14209P29

(12) United States Plant Patent
Hofmann

(10) Patent No.: US PP14,209 P2
(45) Date of Patent: Oct. 7, 2003

(54) GERANIUM PLANT NAMED 'PACVI'

(50) Latin Name: *Pelargonium x hortorum*
Varietal Denomination: 'Pacvi'

(75) Inventor: Christa Hofmann, Grossdittmannsdorf (DE)

(73) Assignee: Elsner Pac Jungpflanzen (DE)

( * ) Notice: Subject to any disclaimer, the term of this patent is extended or adjusted under 35 U.S.C. 154(b) by 0 days.

(21) Appl. No.: 10/292,833

(22) Filed: Nov. 12, 2002

(51) Int. Cl.[7] ..... A01H 5/00
(52) U.S. Cl. ..... Plt./330
(58) Field of Search ..... Plt./330

*Primary Examiner*—Kent Bell
(74) *Attorney, Agent, or Firm*—Webb Ziesenheim Logsdon Orkin & Hanson P.C.

(57) ABSTRACT

A new and distinct zonal geranium plant with distinctive bright red colored flowers above medium green foliage without zonation.

2 Drawing Sheets

Botanical classification: *Pelargonium×hortorum* (zonal geranium).
Varietal denomination: 'Pacvi'.

BACKGROUND OF THE INVENTION

The present invention comprises a new and distinct cultivar of geranium known by the varietal name 'Pacvi'. The new variety was discovered as a seedling in a selective breeding program in Dresden, Germany. The new variety is the result of a combination breeding of unnamed, unpatented selections from breeding group 8K-33. Plants of the new variety exhibit similar habit of their parents, but exhibit darker flower color. The new variety was first asexually reproduced by cuttings in Dresden, Germany in 1999. The new variety has been trial and field tested and has been found to retain its distinctive characteristics and remain true to type through successive propagations.

DESCRIPTION OF THE DRAWING

The accompanying photographic drawings illustrate the new variety, with the color being as nearly true as is possible with color illustrations of this type.

DESCRIPTION OF THE PLANT

Figure 1:
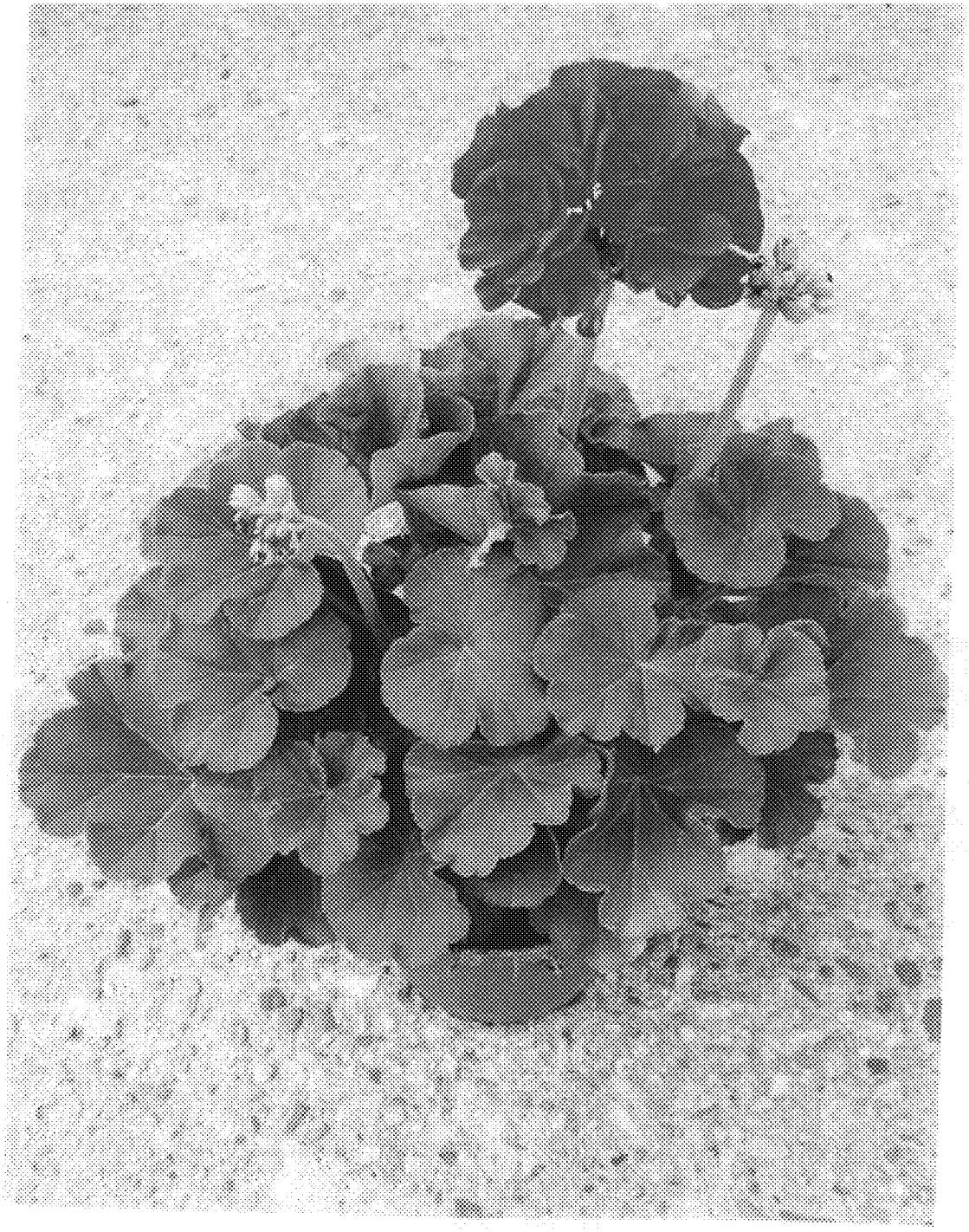
FIG. 1 is a photograph of the plant.
Figure 2:
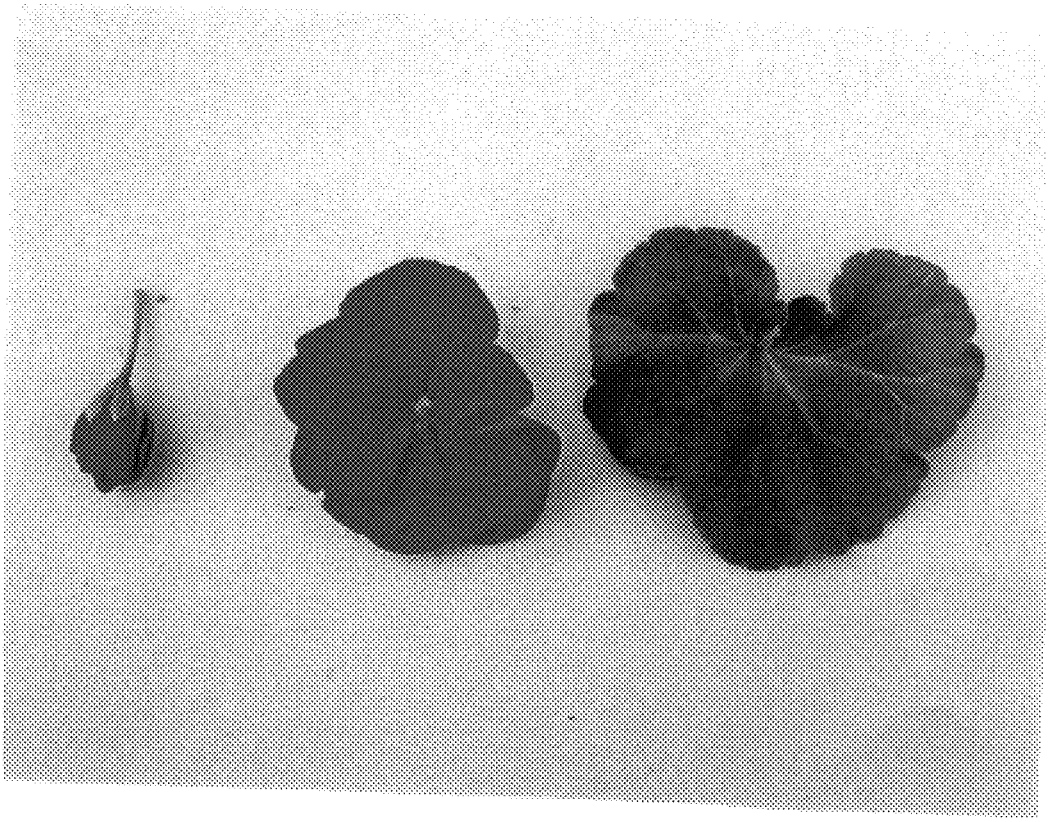
FIG. 2 is a photograph of a bud, flower, and leaf.

The following detailed description sets forth the characteristics of the new cultivar. The data which defines these characteristics were collected from plants propagated in January, potted in February, and grown in a greenhouse and then outdoors in June for data collection in Dresden, Germany. Plants were 9 months old when described. The color readings were taken on a plant under natural indoor light. Color references are primarily to The R.H.S. Colour Chart of The Royal Horticultural Society of London.

PLANT

Form: Upright.
Height: Approximately 17 cm from media surface to top of foliage; approximately 24 cm from media surface to top of umbels.
Strength: Does not require artificial support.

Growth: Erect, well-branched, continuous flowering.
Roots: White; adventive; 3.5 weeks to develop.
Leaves:
- *Arrangement.*—Opposite.
- *Size.*—Length: 4–5 cm. Width: 7.5–9 cm.
- *Shape.*—Overall: Reniform. Base: Partly overlapping. Apex: Rounded.
- *Margin.*—Crenate.
- *Texture.*—Pubescent.
- *Color.*—Upper surface: 137A. Lower surface: 146B. Zonation: Slight, darker than 137A.
- *Ribs and veins.*—Venation: Net-like. Color: 144D.

Petioles:
- *Color.*—143D.
- *Length.*—6–8 cm.

Stem:
- *Color.*—144B.
- *Overall stem length.*—About 13 cm.
- *Internode length.*—1–2 cm.
- *Lateral branch length.*—About 5.5 cm.

THE BUD

Shape when closed:
- *Overall.*—Spherical.
- *Individual bud.*—Round to elliptical.

Size when closed:
- *Overall.*—About 5 cm across cluster.
- *Individual bud.*—1.3 cm long, 1 cm wide.
- *Color.*—45B.

INFLORESCENCE

Size of umbel:
- *Width.*—8.5–10 cm.
- *Length.*—8.5–10 cm.
- *Depth.*—8.5–10 cm.

Borne: Umbel; Flower on pedicel, pedicel on peduncle.
Flowers:
- *Form.*—Zygomorph.
- *Number of flowers per umbel.*—About 60.
- *Size.*—Diameter: About 4.5–5.5 cm. Depth: 1.5–1.7 cm.

Petals:

*Color.*—Upper surface: 45B. Lower surface: 43A. Shape: Overall: Round to oval. Base: Pointed. Apex: Rounded. Size: About 2.7 cm long, 2.6–2.8 cm wide. Margin: Entire. Number per flower: 11–13. Texture and appearance: Smooth.

Sepals:

*Color.*—Upper surface: 143B. Lower surface: 143B.

*Shape.*—Overall: Narrow, pointed. Apex: Pointed. Base: Wider than apex, not pointed.

*Size.*—Length: About 1.1 cm. Width: About 0.3 cm.

Petaloids:

*Quantity.*—0–1 per flower.

*Shape.*—Irregular.

*Color.*—45B upper surface, 43A lower surface.

Pedicel:

*Length.*—About 2.5 cm.

*Color.*—175A.

Peduncle:

*Length.*—About 9.5 cm.

*Color.*—143A.

*Zonation.*—Slight, darker than 137A.

Natural flowering season: Blooms continuously through summer; plant lasts until frost.

Disease/pest resistance: No susceptibility to diseases or pests has been noted to date.

REPRODUCTIVE ORGANS

Stamens:

*Anthers.*—0.1–0.2 cm. in length.

*Filaments.*—Length: About 0.7 cm. Color: 55B. Pollen: 28A; abundant.

Pistils:

*Number.*—One.

*Length.*—About 0.9 cm.

*Stigma.*—45A.

*Style.*—Length: About 0.3 cm. Color: 45A.

*Ovaries.*—Superior, pubescent, about 0.2 cm long, 141C.

Seeds: Rarely present; if present, 5 per flower, 0.4 cm long, colored 165A.

GENERAL CHARACTERISTICS

1. Bright red flower color.
2. Semi-double flower.
3. Tetraploid.
4. Good rooting.
5. Leaves without zonation.
6. Long-lasting.

I claim:

1. A new and distinct variety of geranium plant substantially as shown and described.

* * * * *